(12) United States Patent
Yu et al.

(10) Patent No.: US 10,193,182 B2
(45) Date of Patent: Jan. 29, 2019

(54) NON-AQUEOUS ELECTROLYTE AND LITHIUM SECONDARY BATTERY COMPRISING SAME

(71) Applicant: LG Chem, Ltd., Seoul (KR)

(72) Inventors: Sung-Hoon Yu, Daejeon (KR); Doo-Kyung Yang, Daejeon (KR); Min-Jung Jou, Daejeon (KR); Yoo-Sun Kang, Daejeon (KR); Yoo-Seok Kim, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/544,372

(22) PCT Filed: Mar. 31, 2016

(86) PCT No.: PCT/KR2016/003369
§ 371 (c)(1),
(2) Date: Jul. 18, 2017

(87) PCT Pub. No.: WO2016/159702
PCT Pub. Date: Oct. 6, 2016

(65) Prior Publication Data
US 2018/0013168 A1  Jan. 11, 2018

(30) Foreign Application Priority Data
Mar. 31, 2015 (KR) .................... 10-2015-0045346

(51) Int. Cl.
| H01M 4/58 | (2010.01) |
| H01M 10/052 | (2010.01) |
| H01M 4/36 | (2006.01) |
| H01M 4/485 | (2010.01) |
| H01M 10/0567 | (2010.01) |
| H01M 10/0568 | (2010.01) |
| H01M 10/0569 | (2010.01) |
| C07D 239/30 | (2006.01) |
| C07D 239/32 | (2006.01) |
| C07D 317/36 | (2006.01) |
| H01M 4/02 | (2006.01) |

(52) U.S. Cl.
CPC .......... *H01M 10/052* (2013.01); *H01M 4/36* (2013.01); *H01M 4/485* (2013.01); *H01M 10/0567* (2013.01); *H01M 10/0568* (2013.01); *H01M 10/0569* (2013.01); *C07D 239/30* (2013.01); *C07D 239/32* (2013.01); *C07D 317/36* (2013.01); *H01M 2004/027* (2013.01); *H01M 2004/028* (2013.01); *Y02E 60/122* (2013.01); *Y02T 10/7011* (2013.01)

(58) Field of Classification Search
CPC .......... H01M 10/052; H01M 10/0567; H01M 10/0568; H01M 10/0569; H01M 4/36; H01M 4/485; H01M 2004/027; H01M 2004/028; C07D 239/30; C07D 239/32; C07D 317/36; Y02E 60/122; Y02T 10/7011
See application file for complete search history.

(56) References Cited

U.S. PATENT DOCUMENTS

| 8,906,559 | B2* | 12/2014 | Jung | ................... H01M 4/525 429/324 |
| 2002/0128364 | A1* | 9/2002 | Michot | ................. C08G 65/14 524/401 |
| 2008/0199773 | A1 | 8/2008 | Deguchi et al. | |
| 2011/0129738 | A1 | 6/2011 | Kawashima | |
| 2013/0230770 | A1 | 9/2013 | Oya et al. | |
| 2013/0252113 | A1 | 9/2013 | Yu et al. | |
| 2015/0099192 | A1* | 4/2015 | Yawata | ............. H01M 10/0567 429/332 |

FOREIGN PATENT DOCUMENTS

| CN | 103022556 A | | 4/2013 | |
| JP | 2010-44883 | * | 2/2010 | ........ H01M 10/0567 |
| JP | 2011119097 A | | 6/2011 | |
| KR | 20080077570 A | | 8/2008 | |
| KR | 101225893 B1 | | 1/2013 | |
| KR | 101301082 B1 | | 8/2013 | |
| KR | 20130143083 A | | 12/2013 | |
| KR | 20140037622 A | | 3/2014 | |

OTHER PUBLICATIONS

Search Report from International Application No. PCT/KR2016/003369, dated Jul. 29, 2016.
Extended European Search Report for Application No. EP16773483.9 dated Aug. 21, 2018.

* cited by examiner

*Primary Examiner* — Raymond Alejandro
(74) *Attorney, Agent, or Firm* — Lerner, David, Littenberg, Krumholz & Mentlik, LLP

(57) ABSTRACT

Disclosed are: a non-aqueous electrolyte for a lithium secondary battery containing 1-20 parts by weight of a cyano group-containing pyrimidine-based compound on the basis of 100 parts by weight of an organic solvent; and a lithium secondary battery comprising the same.

17 Claims, 3 Drawing Sheets

NON-AQUEOUS ELECTROLYTE AND LITHIUM SECONDARY BATTERY COMPRISING SAME

CROSS-REFERENCE TO RELATED APPLICATION

This application is a national phase entry under 35 U.S.C. § 371 of International Application No. PCT/KR2016/003369, filed Mar. 31, 2016, which claims priority to Korean Patent Application No. 10-2015-0045346, filed Mar. 31, 2015, the disclosures of which are incorporated herein by reference.

TECHNICAL FIELD

The present disclosure relates to a non-aqueous electrolyte solution for a lithium secondary battery and a lithium secondary battery comprising the same. More particularly, the present disclosure relates to a non-aqueous electrolyte solution for a lithium secondary battery with improved cycle life at room temperature and high temperature, and a lithium secondary battery comprising the same.

BACKGROUND ART

Recently, interest in energy storage technology is increasing day by day. As the application field is extended to mobile phones, camcorders, and laptop computers, and further to energy of electric vehicles, the demand for higher energy density of batteries used as a source of power of electronic devices is growing. Lithium secondary batteries that best satisfy the demand are now being actively studied.

In currently available secondary batteries, lithium secondary batteries developed in the early 1990's are composed of an anode made of carbon material capable of intercalation or deintercalation of lithium ions, a cathode made of lithium-containing oxide, and a non-aqueous electrolyte solution in which an optimal amount of lithium salt is dissolved in a mixed organic solvent.

An average discharge voltage of lithium secondary batteries is about 3.6 to 3.7V that is higher than the discharge voltage of other batteries such as alkali batteries or nickel-cadmium batteries, and this is one of advantages of lithium secondary batteries. For such high operating voltage, the composition of electrolyte solutions that is electrochemically stable in the charge/discharge voltage range of 0 to 4.2V is required. To this end, the electrolyte solution comprises a mixed solvent of cyclic carbonate compounds such as ethylene carbonate and propylene carbonate, and linear carbonate compounds such as dimethyl carbonate, ethyl methyl carbonate and diethyl carbonate as a solvent. As a solute of the electrolyte solutes, lithium salts such as $LiPF_6$, $LiBF_4$ and $LiClO_4$ may be used, and they acts as a source of lithium ions in batteries to allow the lithium batteries to operate.

In the initial charging process of lithium secondary batteries, lithium ions released from a cathode active material, for example, lithium metal oxide, move to an anode active material, for example, graphite, and intercalate into a layer of the anode active material. In this instance, lithium which is highly reactive, reacts with the electrolyte solution and carbon that is a component of the anode active material, graphite, on the surface of the anode active material, yielding a compound such as $Li_2CO_3$, $Li_2O$ and $LiOH$. These compounds form a sort of solid electrolyte interface (SEI) layer on the surface of the anode active material, graphite.

The SEI layer serves as an ion tunnel, allowing only lithium ions to pass through. By virtue of the ion tunnel effect, the SEI layer prevents the organic solvent from intercalation into the layers of the anode active material and from destroying the structure of the anode, the organic solvent having molecules of high molecular weight in the electrolyte solution and moving with lithium ions therein. Accordingly, the contact of the electrolyte solution with the anode active material is avoided, the decomposition of the electrolyte solution does not take place, and the amount of lithium ions in the electrolyte solution is reversibly maintained, allowing stable charging/discharging.

However, in the SEI layer forming reaction, gas such as $CO$, $CO_2$, $CH_4$ and $C_2H_6$ is generated by decomposition of carbonate-based solvents, causing batteries to swell and increase in thickness during charging. If fully charged batteries are kept at high temperature, the SEI layer is slowly destroyed over time due to increased electrochemical energy and thermal energy, and side reactions continue to occur between the exposed surface of the anode and the surrounding electrolyte solution. The gas that is continuously generated increases the internal pressure of batteries, and as a result, the batteries increase in thickness, causing damage to electronic products, such as mobile phones and laptop computers, to which the batteries are applied. That is, safety at high temperature is poor. Furthermore, in common lithium secondary batteries including a large amount of ethylene carbonate, the SEI layer is unstable, leading to severe internal pressure increase of batteries. Moreover, ethylene carbonate has a high freezing point of 37 to 39° C. and is in solid state at room temperature, in turn, has low ionic conductivity at low temperature, and accordingly, lithium batteries using non-aqueous solvents containing a large amount of ethylene carbonate have poor conductivity at low temperature.

To solve the problem, attempts have been made to modify the SEI layer forming reaction by variously changing the ingredient composition of carbonate organic solvents or adding certain additives. However, so far as is known, the change of solvent ingredients or the addition of certain compounds to electrolyte solutions for the purpose of improving the battery performance may improve some performance characteristics, while degrading other performance characteristics.

Accordingly, there is an urgent need for development of the composition of non-aqueous electrolyte solutions for providing lithium secondary batteries that are superior in terms of high rate charging/discharging characteristics, cycle life, and discharging characteristics at low and high temperature.

DISCLOSURE

Technical Problem

The present disclosure is designed to solve the problems of the prior art, and therefore the present disclosure is directed to providing a non-aqueous electrolyte solution for a lithium secondary battery with improved cycle life at room temperature and high temperature, and a lithium secondary battery comprising the same.

Technical Solution

To achieve the technical object, according to one aspect of the present disclosure, there is provided a non-aqueous electrolyte solution for a lithium secondary battery, including an electrolyte salt and an organic solvent, wherein the non-aqueous electrolyte solution further includes a cyano group-containing pyrimidine-based compound represented by the following formula 1, and the cyano group-containing pyrimidine-based compound is present in an amount of 1 to 20 parts by weight per 100 parts by weight of the organic solvent:

[Formula 1]

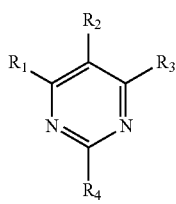

In the formula 1, $R_1$, $R_2$, $R_3$, and $R_4$ are each independently hydrogen, a cyano group, halogen, a substituted or unsubstituted alkyl group having 1 to 10 carbon atoms, or a substituted or unsubstituted alkoxy group having 1 to 10 carbon atoms, in which at least one of $R_1$, $R_2$, $R_3$, and $R_4$ is a cyano group.

According to another aspect of the present disclosure, there is provided a lithium secondary battery including an electrode assembly composed of an anode, a cathode, and a separator interposed between the anode and the cathode, and a non-aqueous electrolyte solution injected in the electrode assembly, wherein said non-aqueous electrolyte solution is the non-aqueous electrolyte solution for a lithium secondary battery.

Advantageous Effects

According to one aspect of the present disclosure, as the lithium secondary battery includes the non-aqueous electrolyte solution containing the cyano group-containing pyrimidine-based compound, the lithium secondary battery has the ability of the cyano group to form a complex on the surface of the cathode, and the abilities of the pyrimidine-based compound to form a thin film on the surface of the anode and to trap metal ions, hence a reduction in battery capacity is noticeably mitigated even after repeated charge/discharge cycles of a few tens to a few hundreds of times at room temperature and high temperature, thereby achieving improved life characteristics and stability of the secondary battery.

MODE FOR CARRYING OUT THE INVENTION

Figure 1:
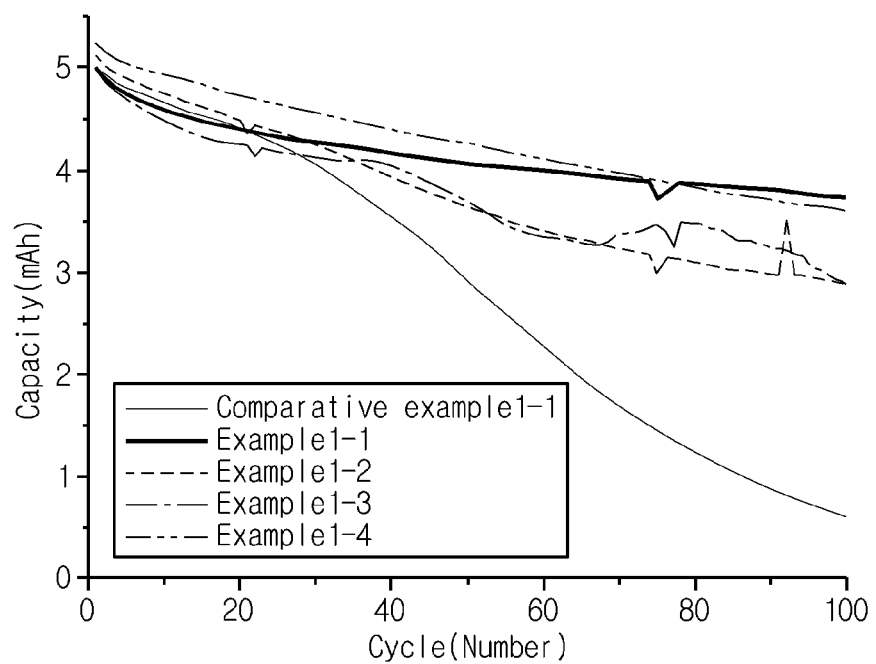
FIG. 1 is a graph showing life characteristics at high temperature of lithium secondary batteries fabricated in examples 2-1 to 2-4 and comparative example 2-1.

Hereinafter, the present disclosure will be described in detail. It should be understood that the terms or words used in the specification and the appended claims shall not be construed as limited to general and dictionary meanings, but interpreted based on the meanings and concepts corresponding to technical aspects of the present disclosure on the basis of the principle that the inventor is allowed to define terms appropriately for the best explanation.

A non-aqueous electrolyte solution for a lithium secondary battery including an electrolyte salt and an organic solvent according to one aspect of the present disclosure further includes a cyano group-containing pyrimidine-based compound represented by the following formula 1, wherein the cyano group-containing pyrimidine-based compound is present in an amount of 1 to 20 parts by weight per 100 parts by weight of the organic solvent:

[Formula 1]

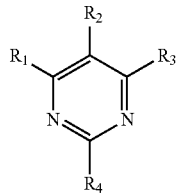

where $R_1$, $R_2$, $R_3$, and $R_4$ are each independently hydrogen, a cyano group, halogen, a substituted or unsubstituted alkyl group having 1 to 10 carbon atoms, or a substituted or unsubstituted alkoxy group having 1 to 10 carbon atoms, in which at least one of $R_1$, $R_2$, $R_3$, and $R_4$ is a cyano group.

Specifically, definition of the substituents is as follows:

The alkl group refers to a straight- or branched-chain saturated monovalent hydrocarbon part having 1 to 10 carbon atoms, 1 to 8 carbon atoms, or 1 to 4 carbon atoms. Examples of the unsubstituted alkyl group include a methyl group, an ethyl group, a propyl group, a butyl group, and a hexyl group. At least one hydrogen atom included in the alkyl group may be substituted by a halogen atom, a hydroxyl group, —SH, a nitro group, a cyano group, a substituted or unsubstituted amino group (—$NH_2$, —NH(R), —N(R')(R''), R' and R'' are each independently an alkyl group having 1 to 10 carbon atoms), an amidino group, hydrazine, or a hydrazone group, a carboxyl group, a sulfonic acid group, a phosphoric acid group, a $C_1$-$C_{20}$ alkyl group, a $C_1$-$C_{20}$ halogenated alkyl group, a $C_1$-$C_{20}$ alkenyl group, a $C_1$-$C_{20}$ alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, or a $C_6$-$C_{20}$ heteroarylalkyl group.

The alkoxy group refer to an oxygen-containing straight- or branched-chain saturated monovalent hydrocarbon part having 1 to 10 carbon atoms, 1 to 8 carbon atoms, or 1 to 4 carbon atoms. Examples of the unsubstituted alkoxy group include methoxy, ethoxy, propoxy, butoxy, and t-butoxy. The alkoxy group may be further substituted by at least one halo atom such as fluoro, chloro or bromo, to provide a haloalkoxy group. Its examples include fluoromethoxy, chloromethoxy, trifluoromethoxy, trifluoroethoxy, fluoroethoxy, and fluoropropoxy. At least one hydrogen atom in the alkoxy group may be substituted by a substituent in the same way as the case of the alkyl group.

Halogen refers to fluorine, chlorine, or bromine.

Generally, when the secondary battery in which the non-aqueous electrolyte solution is injected undergoes repeated charge/discharge cycles, the anode is subject to rapid contraction and expansion, and when an SEI layer formed on the anode is destroyed due to the expansion of the anode during charging, a new SEI layer is formed by decomposition of the electrolyte solution. Due to this, the organic solvent in the non-aqueous electrolyte solution is gradually depleted, and as a result, lithium ions present in the electrolyte solution are consumed, and as the number of cycles increases, the battery capacity gradually decreases.

However, according to an embodiment of the present disclosure, when the cyano group-containing pyrimidine-based compound is introduced into the non-aqueous electrolyte solution, the cyano group-containing pyrimidine-based compound brings into reaction with the anode earlier than a general carbonate-based solvent which is a component of the electrolyte solution, thereby forming a stable and dense thin film on the surface of the anode, which inhibits the continuous decomposition reactions of the carbonate-based solvent with the anode. Therefrom, the capacity reduction of batteries can be minimized and the life characteristics thereof can further be improved, as compared to the case that carbonate-based solvent alone is used.

That is, the pyrimidine-based compound forms a polymeric thin film on the surface of the anode, and nitrogen atoms present in the polymeric thin film have high electron density, making the polymeric thin film have a good metal cation trapping effect. Therefore, metal cations having low electron density can be trapped between the polymeric thin film and the thin film on the electrode that touches the polymeric thin film. As a result, metal cations released from the cathode active material layer are deposited as metal on the surface of the anode.

By the metal cation trapping effect of the pyrimidine-based compound, the discharge rate characteristics can be maintained even after storage at high temperature, thereby providing improved storage performance at high temperature to the secondary battery.

Furthermore, after the electrolyte solution is prepared, the content of water and HF increases over time, and as a consequence, the discharge capacity reduces.

However, when the cyano group-containing pyrimidine-based compound is used in the electrolyte solution, nitrogen atoms of the cyano group-containing pyrimidine-based compound brings into reaction with HF to reduce the content of water and HF, or prevent the content increase of water and HF, thereby inhibiting reduction of discharge capacity in the secondary battery.

In the cyano group-containing pyrimidine-based compound, abundant electrons present in nitrogen and a pyrimidine ring are delocalized, from which radicals generated during electrochemical reactions are stabilized, and a thin film can be easily formed.

Moreover, in an embodiment of the present disclosure, the cyano group bonded to the pyrimidine-based compound forms a strong bond with the cathode surface at high temperature to form a complex, and the formed complex acts as a protective film to block the active site of the cathode surface, thereby preventing some transition metals from being released and deposited on the anode in the charge and discharge process, inhibiting side reactions and gas generation occurring between the electrolyte solution and the cathode, and improving the performance characteristics at high temperature.

The cyano group-containing pyrimidine-based compound is present in an amount of 1 to 20 parts by weight, specifically 1 to 10 parts by weight, and more specifically 1 to 5 parts by weight, per 100 parts by weight of the organic solvent.

When the amount of the cyano group-containing pyrimidine-based compound satisfies such range, the improvement effect of performance at high temperature is fully exerted, and excessive increases in viscosity of the electrolyte solution are prevented, contributing to the characteristics improvement at room temperature and low temperature, and besides, the battery performance degradation during high rate discharging due to excessive resistance increases of the cathode is prevented, and the release of metal ions is inhibited, preventing low voltage phenomena.

According to an embodiment of the present disclosure, in the formula 1, $R_4$ is a cyano group, and $R_1$, $R_2$, and $R_3$ are each independently hydrogen, a cyano group, halogen, a substituted or unsubstituted alkyl group having 1 to 10 carbon atoms, or a substituted or unsubstituted alkoxy group having 1 to 10 carbon atoms. In the case that carbon bridging two nitrogen atoms is substituted by a cyano group in the pyrimidine-based compound, namely, in the case that $R_4$ in the formula 1 is a cyano group, the cyano group coordinates the metal complex with the nitrogen atoms of the pyrimidine ring, so that a better effect can be exerted.

Furthermore, depending on the size or shape of metal ions, in addition to the case that $R_4$ is a cyano group, when at least one of $R_1$, $R_2$, and $R_3$ is a cyano group, the cyano group also coordinates the metal complex with the nitrogen atoms.

The cyano group-containing pyrimidine-based compound includes, but is not limited to, for example, any one selected from 2,4-pyrimidinedicarbonitrile, 2-cyano-5-fluoropyrimidine, 2-cyano-4,6-dimethylpyrimidine, 2-pyrimidinecarbonitrile, 4-cyano-pyrimidine, 2-cyano-4,6-dimethoxypyrimidine, 2,4-dichloro-5-cyano-pyrimidine, 5-cyano-2,4-dihydroxylpyrimidine, and mixtures thereof.

The electrolyte salt included in the non-aqueous electrolyte solution according to one aspect of the present disclosure is a lithium salt. The lithium salt includes, without limitations, those commonly used in electrolyte solutions for lithium secondary batteries. For example, an anion of the lithium salt may be any one selected from the group consisting of $F^-$, $Cl^-$, $Br^-$, $I^-$, $NO_3^-$, $N(CN)_2^-$, $BF_4^-$, $ClO_4^-$, $PF_6^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$ and $(CF_3CF_2SO_2)_2N^-$.

The organic solvent included in the non-aqueous electrolyte solution includes, without limitations, those commonly used in electrolyte solutions for lithium secondary batteries, for example, linear carbonate compounds, cyclic carbonate compounds, ether compounds, ester compounds, and amide compounds. These may be used alone or in a combination form.

Representative examples of the organic solvent includes cyclic carbonate compounds, linear carbonate compounds, or carbonate compounds thereof.

Examples of the cyclic carbonate compounds include at least one selected from the group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate, vinyl ethylene carbonate, and halides thereof. The halides include, but are not limited to, for example, fluoroethylene carbonate (FEC).

According to an embodiment of the present disclosure, especially when the organic solvent includes fluoroethylene carbonate, an amount of the fluoroethylene carbonate is 0.1 to 50 vol %, 1 to 40 vol %, or 3 to 30 vol %, per the total volume of the organic solvent. When the amount of the fluoroethylene carbonate satisfies such range, fluoroethylene carbonate is not used up and is maintained in a uniform amount for long-term cycles, increases in battery costs can be regulated, the battery performance degradation during high rate discharging due to excessive resistance increases of the cathode is prevented, and the electrolyte solution can be uniformly permeate the electrode after it is injected.

Examples of the linear carbonate compounds typically include, but are not limited to, any one selected from the group consisting of dimethyl carbonate (DMC), diethyl carbonate (DEC), dipropyl carbonate, ethyl methyl carbonate (EMC), methyl propyl carbonate, ethyl propyl carbonate, and mixtures thereof.

In particular, in the carbonate compounds, to be exact, the cyclic carbonate compounds, ethylene carbonate and propylene carbonate are high viscosity organic solvents and have a high dielectric constant, allowing the lithium salt in the electrolyte to be more likely to dissociate, and when mixed at an optimal ratio with linear carbonate compounds with low viscosity and low dielectric constant such as dimethyl carbonate and diethyl carbonate, electrolyte solutions with higher electrical conductivity will be obtained.

Furthermore, among the exemplary organic solvents, the ether compounds include, but are not limited to, any one selected from the group consisting of dimethyl ether, diethyl ether, dipropyl ether, methyl ethyl ether, methyl propyl ether, ethyl propyl ether, and mixtures thereof.

In addition, among the exemplary organic solvents, the ester compounds include, but are not limited to, any one selected from the group consisting of methyl acetate, ethyl acetate, propyl acetate, methyl propionate, ethyl propionate, propyl propionate, butyl propionate, γ-butyrolactone, γ-valerolactone, γ-caprolactone, σ-valerolactone, ε-caprolactone, and mixtures thereof.

The non-aqueous electrolyte solution for a lithium secondary battery of the present disclosure may further include SEI layer-forming additives without deviating from the principle of the present disclosure. The SEI layer-forming additives that can be used in the present disclosure include, but is not limited thereto, a cyclic sulfite, a saturated sultone, an unsaturated sultone, and a non-cyclic sulfone. These may be used alone or in a combination form. Among the aforementioned cyclic carbonates, vinylene carbonate, vinyl ethylene carbonate, and fluoroethylene carbonate may be also used as the SEI layer-forming additives to improve the battery life.

Examples of the cyclic sulfite include ethylene sulfite, methyl ethylene sulfite, ethyl ethylene sulfite, 4,5-dimethyl ethylene sulfite, 4,5-diethyl ethylene sulfite, propylene sulfite, 4,5-dimethyl propylene sulfite, 4,5-diethyl propylene sulfite, 4,6-dimethyl propylene sulfite, 4,6-diethyl propylene sulfite and 1,3-butylene glycol sulfite. Examples of the saturated sultone include 1,3-propane sultone and 1,4-butane sultone. Examples of the unsaturated sultone include ethene sultone, 1,3-propene sultone, 1,4-butene sultone and 1-methyl-1,3-propene sultone. Examples of the non-cyclic sulfone include divinyl sulfone, dimethyl sulfone, diethyl sulfone, methyl ethyl sulfone and methyl vinyl sulfone.

The SEI layer-forming additives are present in an optimal amount depending on its specific type, and for example, the SEI layer-forming additives are present in an amount of 0.01 to 10 parts by weight per 100 parts by weight of the non-aqueous electrolyte solution.

Although a stable thin film is formed on the anode by the cyano group-containing pyrimidine-based compound, solids may be produced by the additives used, and in this case, the performance improvement effect of thin film formation may be reduced.

In this regard, among the exemplary additives, when the cyclic sulfite or the unsaturated sultone, in particular, ethylene sulfite and 1,3-propane sultone is used, reactivity with the cyano group-containing pyrimidine-based compound is low, and solids are not produced.

The non-aqueous electrolyte solution may be used per se in the form of a liquid electrolyte, or a gel polymer immersed in polymer for the electrolyte of the lithium secondary battery.

The non-aqueous electrolyte solution according to one aspect of the present disclosure may be obtained by mixing the non-aqueous solvent and fluoroethylene carbonate with the electrolyte salt, and adding and dissolving the pyrimidine-based compound represented by the above formula 1.

In this instance, the compounds being added to the non-aqueous solvent and electrolyte solution are subject to pre-purification before using within a range which will not substantially deteriorate productivity, so as to have little or no impurity.

When air or carbon dioxide, for example, is included in the non-aqueous electrolyte solution, gas generation by decomposition of the electrolyte solution may be inhibited, or battery characteristics including long-term cycling characteristics and charge sustaining characteristics may be further improved.

For the improvement of charge/discharge characteristics at high temperature, as the non-aqueous electrolyte solution, an electrolyte solutions comprising carbon dioxide dissolved therein may be used. The carbon dioxide may be dissolved in an amount of 0.001 wt % or more, 0.05 wt % or more, or 0.2 wt % or more per the weight of the non-aqueous electrolyte solution, and carbon dioxide may be dissolved in the non-aqueous electrolyte solution until it is saturated therein.

Furthermore, according to one aspect of the present disclosure, there is provided a lithium secondary battery including an electrode assembly composed of an anode, a cathode and a separator interposed between the cathode and the anode, and a non-aqueous electrolyte solution injected in the electrode assembly, wherein the non-aqueous electrolyte solution is the aforementioned non-aqueous electrolyte solution for a lithium secondary battery.

The cathode, the anode, and the separator of the electrode assembly include those commonly used in the fabrication of lithium secondary batteries.

The cathode has a structure in which a cathode layer including a cathode active material, a conductive material and a binder is supported on one or two surfaces of a current collector.

The cathode active material preferably includes lithium-containing transition metal oxide, and for example, includes any one selected from the group consisting of $Li_xCoO_2$ ($0.5<x<1.3$), $Li_xNiO_2$($0.5<x<1.3$), $Li_xMnO_2$($0.5<x<1.3$), $Li_xMn_2O_4$($0.5<x<1.3$), $Li_x(Ni_aCo_bMn_c)O_2$($0.5<x<1.3$, $0<a<1$, $0<b<1$, $0<c<1$, $a+b+c=1$), $Li_xNi_{1-y}Co_yO_2$ ($0.5<x<1.3$, $0<y<1$), $Li_xCo_{1-y}Mn_yO_2$($0.5<x<1.3$, $0\le y<1$), $Li_xNi_{1-y}Mn_yO_2$($0.5<x<1.3$, $0\le y<1$), $Li_x(Ni_aCo_bMn_c)O_4$ ($0.5<x<1.3$, $0<a<2$, $0<b<2$, $0<c<2$, $a+b+c=2$), $Li_xMn_{2-z}Ni_zO_4$($0.5<x<1.3$, $0<z<2$), $Li_xMn_{2-z}Co_zO_4$($0.5<x<1.3$, $0<z<2$), $Li_xCoPO_4$($0.5<x<1.3$) and $LixFePO_4$($0.5<x<1.3$), or mixtures thereof.

The lithium-containing transition metal oxide may be coated with metal such as aluminum (Al) or metal oxide. In addition to the lithium-containing transition metal oxide, a sulfide, a selenide, and a halide may be used.

The conductive material includes, without limitations, any electronically conductive material so long as it does not cause any chemical change in electrochemical devices. Generally, the conductive material includes carbon black, graphite, carbon fibers, carbon nanotubes, metal powder, conductive metal oxide, and organic conductive materials, and examples of commercial conductive materials currently on the market include acetylene black (from Chevron Chemical Company or Gulf Oil Company), Ketjen Black EC (from Armak Company), Vulcan XC-72 (from Cabot Company), and Super P (from MMM Carbon Company). For example, acetylene black, carbon black and graphite may be used.

The anode has a structure in which an anode layer including an anode active material and a binder is supported on one or two surfaces of a current collector.

The anode active material includes carbon materials, lithium metals, and metal compounds that are generally capable of intercalation and deintercalation of lithium ions, and mixtures thereof.

Specifically, the carbon materials include low-crystalline carbon and high-crystalline carbon. The low-crystalline carbon typically includes soft carbon and hard carbon, and the high-crystalline carbon typically include natural graphite, Kish graphite, pyrolytic carbon, mesophase pitch based carbon fiber, meso-carbon microbeads, mesophase pitches, and carbon calcined at high temperature such as petroleum or coal tar pitch derived cokes.

The metal compounds may be compounds containing at least one metal element selected from Si, Ge, Sn, Pb, P, Sb, Bi, Al, Ga, In, Ti, Mn, Fe, Co, Ni, Cu, Zn, Ag, Mg, Sr and Ba, or mixtures of the compounds. The metal compounds may be used in any form, for example, substances, alloys, oxides ($TiO_2$, $SnO_2$, etc.), nitrides, sulfides, borides, and alloys with lithium, and substances, alloys, oxides, and alloys with lithium contribute to high capacity. Among them, at least one element selected from Si, Ge, and Sn may be included, and inclusion of at least one element selected from Si and Sn contributes to higher battery capacity.

The binder used in the cathode and the anode has functions to hold the cathode and anode active materials on the current collector and interconnect the active materials, and any common binder can be used.

For example, various types of binders including vinylidene fluoride-hexafluoropropylene copolymer (PVDF-co-HFP), polyvinylidene fluoride, polyacrylonitrile, polymethylmethacrylate, styrene butadiene rubber (SBR), and carboxymethyl cellulose (CMC) may be used.

The current collector used in the cathode and anode may be made of any metal having high conductivity to which a slurry of the active material is easily adhered, as long as it is not reactive within the voltage range of the battery. Specifically, non-limiting examples of the current collector for the cathode include foils made of aluminum, nickel, and combinations thereof, and non-limiting examples of the current collector for the anode include foils made of copper, gold, nickel or copper alloy, or combinations thereof. The current collector may be used in a laminated form of substrates made of such materials.

Each of the cathode and the anode may be prepared by mixing an active material, a conductive material, a binder, and a solvent to prepare a mixed electrode material and applying the mixed electrode material on a current collector, followed by drying, compression molding, and heat treatment under vacuum at the temperature of 50° C. to 250° C. for about 2 hours.

Furthermore, the thickness of the electrode layer of the cathode is 30 to 120 μm or 50 to 100 μm on one surface of the current collector, and the thickness of the electrode layer of the anode is 1 to 100 μm or 3 to 70 μm on one surface of the current collector. When the electrode layers of the cathode and the anode satisfy these thickness ranges, it is possible to ensure a sufficient amount of active materials in the electrode layer, thereby preventing the battery capacity from being lowered and improving cycling and rate characteristics.

Furthermore, the separator includes, but is not limited thereto, general porous polymer films conventionally used for separators, for example, porous polymer films made of polyolefin-based polymers such as ethylene homopolymer, propylene homopolymer, ethylene/butene copolymer, ethylene/hexene copolymer and ethylene/methacrylate copolymer, used singly or in combination, or general porous non-woven fabrics, for example, non-woven fabrics made of glass fibers having a high melting point or polyethylene terephthalate fibers.

Furthermore, the separator may include the porous polymer film, a porous substrate such as a porous non-woven fabric, and a porous coating layer including inorganic particles and a binder on at least one surface of the porous substrate.

The lithium secondary battery of the present disclosure has no limitation on its shape, but may be in a cylindrical shape using a can, a prismatic shape, a pouch shape or a coin shape.

Hereinafter, the present disclosure will be described in detail with reference to the following examples. However, the examples according to the present disclosure may be modified in many different forms, and the scope of the present disclosure shall not be construed as being limited to the following examples. The examples of the present disclosure are provided to persons having ordinary skill in the art for full and complete understanding of the present disclosure.

Preparation of Non-Aqueous Electrolyte Solution

EXAMPLE 1-1

Fluoroethylene carbonate (FEC), propylene carbonate (PC), and ethylmethyl carbonate (EMC) were mixed at a ratio of 30 vol %, 10 vol %, and 60 vol %, respectively, to prepare a mixture of organic solvents. Subsequently, 1 part by weight of 2,4-pyrimidinedicarbonitrile and 2 parts by weight of 1,3-propane sultone were further added per 100 parts by weight of the mixture of organic solvents, and $LiPF_6$ was dissolved such that the concentration is 1M, to prepare a non-aqueous electrolyte solution.

EXAMPLE 1-2

A non-aqueous electrolyte solution was prepared by the same method as example 1-1 except that 2-cyano-5-fluoropyrimidine was used instead of 2,4-pyrimidinedicarbonitrile.

EXAMPLE 1-3

A non-aqueous electrolyte solution was prepared by the same method as example 1-1 except that 2-cyano-4,6-dimethylpyrimidine was used instead of 2,4-pyrimidinedicarbonitrile.

EXAMPLE 1-4

A non-aqueous electrolyte solution was prepared by the same method as example 1-1 except that 2-pyrimidinecarbonitrile was used instead of 2,4-pyrimidinedicarbonitrile.

EXAMPLE 1-5

A non-aqueous electrolyte solution was prepared by the same method as example 1-1 except that 2 parts by weight of 2-pyrimidinecarbonitrile was used instead of 1 part by weight of 2,4-pyrimidinedicarbonitrile.

COMPARATIVE EXAMPLE 1-1

A non-aqueous electrolyte solution was prepared by the same method as example 1-1 except that 2,4-pyrimidinedicarbonitrile was not used.

COMPARATIVE EXAMPLE 1-2

A non-aqueous electrolyte solution was prepared by the same method as example 1-1 except that 0.5 parts by weight of 2-pyrimidinecarbonitrile was used instead of 1 part by weight of 2,4-pyrimidinedicarbonitrile.

Fabrication of Lithium Secondary Battery

EXAMPLE 2-1

(1) Manufacture of Cathode 90 parts by weight of lithium cobalt composite oxide as cathode active material particles, 5 parts by weight of carbon black as a binder, and 5 parts by weight of polyvinylidenefluoride (PVdF) as a binder were added to 40 parts by weight of N-methyl-2 pyrrolidone (NMP) used as a solvent to prepare a cathode active material slurry. The cathode active material slurry was applied to a 100 μm thick aluminum (Al) thin film for a cathode current collector, followed by drying and roll pressing, to manufacture a cathode.

(2) Manufacture of Anode 95 parts by weight of natural graphite as an anode active material, 2 parts by weight of polyvinylidenefluoride (PVdF) as a binder, 3 parts by weight of carbon black as a conductive material were added to 100 parts by weight of N-methyl-2 pyrrolidone (NMP) solvent to prepare an anode active material slurry. The anode active material slurry was applied to a 90 μm thick copper (Cu) thin film for an anode current collector, followed by drying and roll pressing, to manufacture an anode.

(3) Fabrication of Lithium Secondary Battery

Using the cathode and anodes manufactured by the above method and a polyethylene porous film, a pouch-type battery was fabricated by a common method, and the non-aqueous electrolyte solution of example 1-1 previously prepared was injected to produce a lithium secondary battery.

EXAMPLE 2-2

A lithium secondary battery was fabricated by the same method as example 2-1 was repeated except that the non-aqueous electrolyte solution prepared in example 1-2 was used.

EXAMPLE 2-3

A lithium secondary battery was fabricated by the same method as example 2-1 was repeated except that the non-aqueous electrolyte solution prepared in example 1-3 was used.

EXAMPLE 2-4

A lithium secondary battery was fabricated by the same method as example 2-1 was repeated except that the non-aqueous electrolyte solution prepared in example 1-4 was used.

EXAMPLE 2-5

A lithium secondary battery was fabricated by the same method as example 2-1 was repeated except that the non-aqueous electrolyte solution prepared in example 1-5 was used.

COMPARATIVE EXAMPLE 2-1

A lithium secondary battery was fabricated by the same method as example 2-1 was repeated except that the non-aqueous electrolyte solution prepared in comparative example 1-1 was used.

COMPARATIVE EXAMPLE 2-2

A lithium secondary battery was fabricated by the same method as example 2-1 was repeated except that the non-aqueous electrolyte solution prepared in comparative example 1-2 was used.

Evaluation of Characteristics of Lithium Secondary Battery

Life Characteristics at High Temperature

The lithium secondary batteries (battery capacity: 5.5 mAh) fabricated in examples 2-1 to 2-4 and comparative example 2-1 were charged at 60° C. with a constant current of 0.7 C up to 4.35V and then charged with a constant voltage of 4.35V, and the charging procedure was stopped when the charging current reached 0.275 mA. After the batteries were left for 10 minutes, the batteries were discharged with a constant current of 0.5 C up to 3.0 V. After 100 charge/discharge cycles, the battery capacity was measured and shown in FIG. 1. Here, C denotes a charging/discharging current rate of batteries, C-rate, in ampere (A), and is usually expressed as a rate of the battery capacity. Accordingly, in the batteries fabricated above, 1 C represents the current of 5.5 mA.

Referring to FIG. 1, it can be seen that the lithium secondary batteries of examples 2-1 to 2-4 including the electrolyte solution containing the cyano group-containing pyrimidine-based compound all show superior life characteristics at high temperature, as compared with the lithium secondary battery of comparative example 2-1 including the electrolyte solution containing no cyano group-containing pyrimidine-based compound.

Thin Film Forming Capability on Anode Surface

Figure 2:
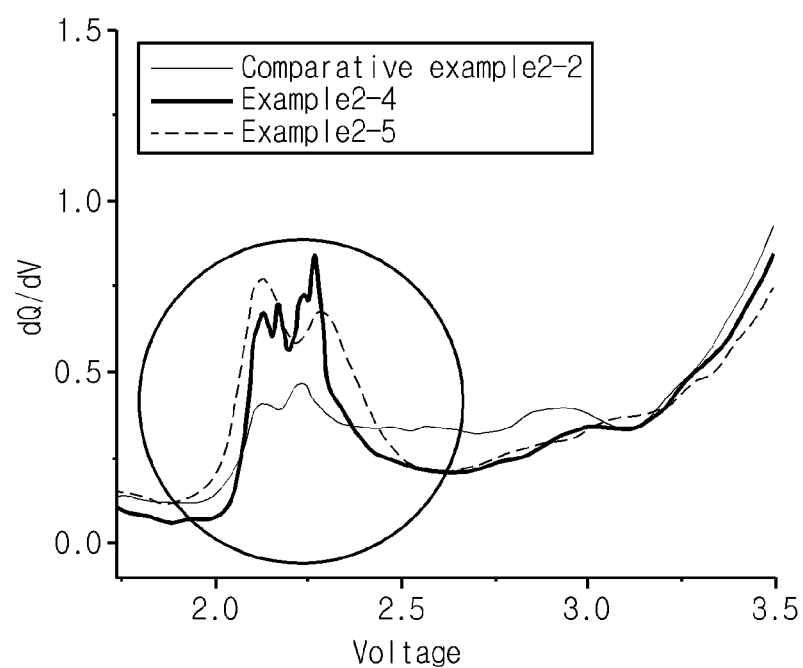
FIG. 2 is a graph showing dQ/dV vs voltage (V) curves for the first charge of lithium secondary batteries fabricated in examples 2-4 and 2-5 and comparative example 2-2.

The differential capacity (dQ/dV) vs voltage (V) obtained in the first charge process of the lithium secondary batteries (battery capacity (5.5 mAh) fabricated in examples 2-4 and 2-5, and comparative example 2-2 under the condition of 0.1 C CC/CV is shown in FIG. 2.

In FIG. 2, dQ/dV peaks around 2.4V represent the extent to which 2-pyrimidinecarbonitrile forms a thin film on the anode surface, and in this instance, the intensity of the dQ/dV peaks around 2.4V and the extent of the thin film forming reaction have a proportional relationship.

As a result of plotting the differential capacity (dQ/dV) vs voltage (V) with varying 2-pyrimidinecarbonitrile and additives in electrolyte solutions of the same composition, it was found that the intrinsic reaction voltage of 2-pyrimidinecarbonitrile was around 2.4V.

The peaks around 2.4V correspond to the peak appearing when 2-pyrimidinecarbonitrile is decomposed, and a stronger reaction consumes more electrons, showing a larger peak. Accordingly, the extent of the thin film forming reaction can be evaluated from the intensity of the dQ/dV peaks.

Referring to FIG. 2, it can be seen that examples 2-4 and 2-5 each including 1 part by weight and 2 parts by weight of 2-pyrimidinecarbonitrile dramatically increased in the thin film forming capacity on the anode surface, when compared to comparative example 2-2 including 0.5 parts by weight of 2-pyrimidinecarbonitrile.

Life Characteristics at High Temperature

The lithium secondary batteries (Capacity: 5.5 mAh) fabricated in examples 2-4 and 2-5 and comparative example 2-2 were charged at 65° C. with a constant current of 1.0 C up to 4.35V and then charged with a constant voltage of 4.35V, and the charging procedure was stopped when the charging current reached 0.275 mA. After the batteries were left for 10 minutes, the batteries were discharged with a constant current of 0.5 C up to 3.0V. After 50 charge/discharge cycles, the battery capacity was measured and shown in FIG. 3. Here, C denotes a charging/discharging current rate, C-rate, in ampere (A), and is usually expressed as a rate of the battery capacity. Accordingly, in the batteries fabricated above, 1 C represents the current of 5.5 mA.

Figure 3:
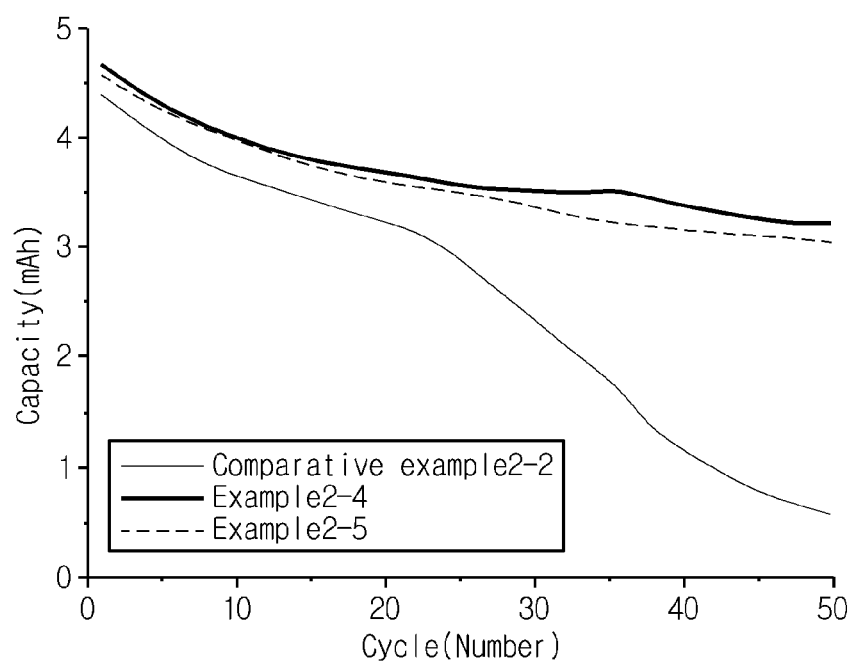
FIG. 3 is a graph showing life characteristics at high temperature of lithium secondary batteries fabricated in examples 2-4 and 2-5 and comparative example 2-2.

Referring to FIG. 3, it can be seen that the lithium secondary batteries of examples 2-4 and 2-5 including the electrolyte solution containing 1 part by weight or greater of cyano group-containing pyrimidine-based compound all show much superior life characteristics at high temperature, as compared with the lithium secondary battery of comparative example 2-2 including the electrolyte solution containing 0.5 parts by weight of cyano group-containing pyrimidine-based compound.

What is claimed is:

1. A non-aqueous electrolyte solution for a lithium secondary battery, comprising an electrolyte salt and an organic solvent, wherein the non-aqueous electrolyte solution further comprises a cyano group-containing pyrimidine-based compound represented by the following formula 1, and the cyano group-containing pyrimidine-based compound is present in an amount of 1 to 20 parts by weight per 100 parts by weight of the organic solvent:

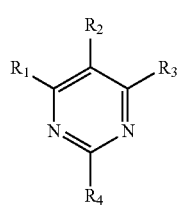

[Formula 1]

where $R_1$, $R_2$, $R_3$ and $R_4$ are each independently hydrogen, a cyano group, halogen, a substituted or unsubstituted alkyl group having 1 to 10 carbon atoms, or a substituted or unsubstituted alkoxy group having 1 to 10 carbon atoms, in which at least one of $R_1$, $R_2$, $R_3$ and $R_4$ is a cyano group.

2. The non-aqueous electrolyte solution for a lithium secondary battery according to claim 1, wherein in the formula 1, $R_4$ is a cyano group, and $R_1$, $R_2$, and $R_3$ are each independently hydrogen, a cyano group, halogen, a substituted or unsubstituted alkyl group having 1 to 10 carbon atoms, or a substituted or unsubstituted alkoxy group having 1 to 10 carbon atoms.

3. The non-aqueous electrolyte solution for a lithium secondary battery according to claim 1, wherein the cyano group-containing pyrimidine-based compound is any one selected from the group consisting of 2,4-pyrimidinedicarbonitrile, 2-cyano-5-fluoropyrimidine, 2-cyano-4,6-dimethylpyrimidine, 2-pyrimidinecarbonitrile, 4-cyano-pyrimidine, 2-cyano-4,6-dimethoxypyrimidine, 2,4-dichloro-5-cyano-pyrimidine, 5-cyano-2,4-dihydroxylpyrimidine, and mixtures thereof.

4. The non-aqueous electrolyte solution for a lithium secondary battery according to claim 1, wherein the electrolyte salt is a lithium salt.

5. The non-aqueous electrolyte solution for a lithium secondary battery according to claim 4, wherein an anion of the lithium salt is any one selected from the group consisting of $F^-$, $Cl^-$, $Br^-$, $I^-$, $NO_3^-$, $N(CN)_2^-$, $BF_4^-$, $ClO_4^-$, $PF_6^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$ and $(CF_3CF_2SO_2)_2N^-$.

6. The non-aqueous electrolyte solution for a lithium secondary battery according to claim 1, wherein the organic solvent includes any one selected from the group consisting of a linear carbonate compound, a cyclic carbonate compound, an ether compound, an ester compound, an amide compound and mixtures thereof.

7. The non-aqueous electrolyte solution for a lithium secondary battery according to claim 6, wherein the linear carbonate compound includes any one selected from the group consisting of dimethyl carbonate, diethyl carbonate, dipropyl carbonate, ethyl methyl carbonate, methyl propyl carbonate, ethyl propyl carbonate, and mixtures thereof.

8. The non-aqueous electrolyte solution for a lithium secondary battery according to claim 6, wherein the cyclic carbonate compound includes at least one selected from the group consisting of ethylene carbonate, propylene carbonate, 1,2-butylene carbonate, 2,3-butylene carbonate, 1,2-pentylene carbonate, 2,3-pentylene carbonate, vinylene carbonate, vinyl ethylene carbonate, and halides thereof.

9. The non-aqueous electrolyte solution for a lithium secondary battery according to claim 8, wherein the halide is fluoroethylene carbonate.

10. The non-aqueous electrolyte solution for a lithium secondary battery according to claim 6, wherein the ether compound includes any one selected from the group consisting of dimethyl ether, diethyl ether, dipropyl ether, methyl ethyl ether, methyl propyl ether, ethyl propyl ether, and mixture thereof.

11. The non-aqueous electrolyte solution for a lithium secondary battery according to claim 1, which further comprises any one selected from the group consisting of a cyclic sulfite, a saturated sultone, an unsaturated sultone and a non-cyclic sulfone, and mixtures thereof.

12. A lithium secondary battery comprising an electrode assembly composed of an anode, a cathode, and a separator interposed between the cathode and the anode, and a non-aqueous electrolyte solution injected in the electrode assembly, wherein the non-aqueous electrolyte solution is the non-aqueous electrolyte solution for a lithium secondary battery according to claim 1.

13. The lithium secondary battery according to claim 12, wherein the anode has an anode active material layer including lithium metal, a carbon material, a metal compound, or mixtures thereof.

14. The lithium secondary battery according to claim 13, wherein the metal compound is compounds containing at least one metal element selected from the group consisting of Si, Ge, Sn, Pb, P, Sb, Bi, Al, Ga, In, Ti, Mn, Fe, Co, Ni, Cu, Zn, Ag, Mg, Sr and Ba, or mixtures of the compounds.

15. The lithium secondary battery according to claim 12, wherein the cathode has a cathode layer including lithium-containing oxide.

16. The lithium secondary battery according to claim 15, wherein the lithium-containing oxide is a lithium-containing transition metal oxide.

17. The lithium secondary battery according to claim 16, wherein the lithium-containing transition metal oxide is any one selected from the group consisting of $LiCoO_2$, $LiNiO_2$, $LiMnO_2$, $LiMn_2O_4$, $Li(Ni_aCo_bMn_c)O_2(0<a<1, 0<b<1, 0<c<1, a+b+c=1)$, $LiNi_{1-y}Co_yO_2$, $LiCo_{1-y}Mn_yO_2$, $LiNi_{1-y}Mn_yO_2(0\leq y<1)$, $Li(Ni_aCo_bMn_c)O_4(0<a<2, 0<b<2, 0<c<2, a+b+c=2)$, $LiMn_{2-z}Ni_zO_4$, $LiMn_{2-z}Co_zO_4(0<z<2)$, $LiCoPO_4$, $LiFePO_4$, and mixtures thereof.

* * * * *